United States Patent [19]

Wu

[11] Patent Number: 5,079,385
[45] Date of Patent: Jan. 7, 1992

[54] CONVERSION OF PLASTICS
[75] Inventor: Margaret M. Wu, Belle Mead, N.J.
[73] Assignee: Mobil Oil Corp., Fairfax, Va.
[21] Appl. No.: 394,901
[22] Filed: Aug. 17, 1989
[51] Int. Cl.$^5$ ................................................. C07C 1/00
[52] U.S. Cl. .................................... 585/241; 585/439; 585/648; 585/653; 585/752
[58] Field of Search ............... 585/241, 439, 648, 653, 585/752

[56] References Cited

U.S. PATENT DOCUMENTS

| | | | |
|---|---|---|---|
| 3,985,820 | 10/1976 | Albright et al. | 585/241 |
| 4,108,730 | 8/1978 | Chen et al. | 585/241 |
| 4,251,500 | 2/1981 | Morita et al. | 585/241 |
| 4,584,421 | 4/1986 | Saito et al. | 585/241 |
| 4,851,601 | 7/1989 | Fukuda et al. | 585/241 |

OTHER PUBLICATIONS

Pines, Herman, *The Chemistry of Catalytic Hydrocarbon Conversions*, Academic Press; New York (1981), pp. 1 and 33.

Primary Examiner—Anthony McFarlane
Assistant Examiner—Nhat Phan
Attorney, Agent, or Firm—Alexander J. McKillop; Charles J. Speciale; Lori F. Cuomo

[57] ABSTRACT

A process for converting solid plastic materials, preferably waste materials, into usable lower molecular weight hydrocarbonaceous materials by reacting such plastic materials at elevated temperatures in effective contact with an acidic catalyst comprising at least one zeolite having acid activity.

20 Claims, No Drawings

CONVERSION OF PLASTICS

This invention relates to the conversion of plastic, particularly waste plastic products, into environmentally less detrimental materials. It more particularly refers to the conversion of relatively inert polymeric materials, which are slow to degrade into environmentally safe, disposable materials, into such lighter hydrocarbonaceous products which are more easily disposed of in a relatively environmentally safe manner.

BACKGROUND OF THE INVENTION

Each year, very large quantities of various plastic products are produced. While many of these products find relatively permanent use in our industrial society, the overwhelming preponderance thereof fall into the disposable-use category. Typical of these disposable-use type of products are fast food containers, supermarket plastic bags, dry cleaner plastic bags, agricultural plastic film mulches and the like.

It is well known that most plastics have found wide use at least partially because of their inertness. In fact, it is this same general chemical inertness which has in recent years started to cause a disposal problem of such magnitude, that some states have seriously contemplated banning, or at least significantly reducing, the use of "plastic" fast food containers, egg containers, milk containers, carbonated beverage containers and the like.

Unfortunately most of these products do not environmentally decay at any appreciable rate and thus they litter the road sides and fill the landfills. Furthermore, most of these polymers and products made therefrom do not incinerate very well. They tend to char, rather than burn, unless the incineration is at very high temperatures. Often, incineration gives off noxious fumes. This is economically unattractive; even more so because these plastics normally have a very high energy content in terms of their compositions, and should be a valuable energy source rather than an energy drain.

Still further, many plastics are made of chemical components which retard burning, for example polyvinyl chloride, polyvinylidene chloride, polytetrafluoroethylene, polycarbonates, and other similar materials. Many of these plastics, if burned in an uncontrolled manner, can give off various and environmentally undesirable by products, such as chlorinated or fluorinated hydrocarbons and acids.

SUMMARY OF THE INVENTION

It has now been discovered that plastic products in general, and highly hydrocarbonaceous plastics in particular, such as for example polyolefins as exemplified by polyethylene, polypropylene, and polystyrene, can be reacted, in contact with acidic zeolite catalysts, to produce substantially lower molecular weight products. These lower molecular weight products have all the usual uses conventionally attributed to them.

Thus, these polymers can be converted by zeolitic acid and/or metal catalysis into various useful products, such as gasoline, distillate boiling range heating or Diesel oil, lubricants and/or light saturated or unsaturated gaseous materials. The nature of the product produced will, to a large measure, be a function of the particular zeolitic catalyst used. Indeed, there seems to be a strong correlation between the pore size of the zeolitic catalyst used and the nature of the product produced. Further, there is an apparent correlation between the acid activity of the zeolitic catalyst used and the environment of the conversion on the one hand, and the nature of the products produced. It now appears that what was formerly thought of as environmentally difficult waste may well be a valuable energy source.

DETAILED DESCRIPTION OF THE INVENTION

It appears that the practice of this invention is not limited to any particular zeolite or class of zeolites. Such limitations as exist are more generic in nature. Thus, the selected zeolite catalyst must have sufficient acid activity to catalyze the cracking and hydrogen transfer reactions involved. Further, the essential nature of the selected zeolite crystal structure and composition must be such as to be able to withstand the rigors of this type of service without substantial deterioration. Since the reactions being catalyzed according to this invention are in the nature of cracking reactions, the zeolitic catalysts will need periodic regeneration in order to remove carbon, which accumulates during cracking, therefrom. By burning off this accumulated carbon, it is possible to generate much or all of the heat necessary to support endothermic cracking reactions.

Zeolites suitable for use in this invention range in pore size from those designated as small pore, i.e. those having 8 tetrahedra constituting their pore defining ring; through those of intermediate pore size, i.e. those having 10 tetrahedra, or comprise puckered 12 tetrahedra, in their pore defining ring; and include so-called large pore zeolites such as those having 12 or more tetrahedra in their pore defining ring structures. Small pore zeolites generally are those having pore/channel diameters of less than about 5 angstroms. Intermediate pore zeolites have pore/channel diameters of about 5 to 7 angstroms. Large pore zeolites are generally characterized as those having pore/channel defining diameters of greater than about 7 angstroms and include swollen, layered acidic refractory materials.

It should be understood that the nature of the desired product produced by plastic cracking is to a large measure determined by the pore size of the zeolitic catalyst. Generally speaking, small pore zeolitic catalysts will produce more products having less than about six(6) carbon atoms in their structure. This is because such small pores will only permit the passage therethrough of these small molecules. Thus, cracking with erionite, ZSM-34, or other representative small pore zeolitic catalysts, will produce more $C_5$-hydrocarbonaceous gases. In the event that a small pore zeolite catalyst is used that has high outside surface acid activity, this limitation will not apply. In that case, the product produced by cracking plastic materials will contain a large amount of $C_5{}^+$ hydrocarbons.

By contrast, catalyzing plastic cracking with intermediate pore zeolitic catalysts will generally produce a product distribution in which naphtha boiling range products, such as $C_6$ to $C_{12}$ hydrocarbons, will predominate. Depending upon the particular nature of the feed, these products may be higher or lower octane gasoline usable directly in the gasoline pool or may constitute a suitable reforming feed.

Catalyzing plastic cracking with large pore zeolites will generally yield higher boiling range products, such as fuel oil, Diesel oil, lubricants and other materials of higher boiling range which may find use as a feed component to conventional catalytic cracking or hydrocracking.

It is important, in selecting the particular zeolitic catalyst to be used in this process, to evaluate not only the desired product boiling range and composition, but the nature of the feed plastic as well. Not only will the zeolite pore size effectively determine and control the product which will be made by this process, but it will also determine the range of feed materials that can be efficiently processed in this process. Thus, a small pore zeolitic catalyst must necessarily have plastic molecules which will fit into its pore system to work on. If the feed molecules are too big, they cannot get into the zeolitic pore system where the acidic cracking activity predominantly resides. These large plastics molecules can only be cracked by the residual outside surface (as opposed to the surface within the pore system of the zeolite) acidity of the small pore zeolite structure or other, large pore structures which may coexist with the small pore crystal in the same overall structure, and therefore will not be processed efficiently by small pore zeolites to any substantial extent.

It should then be apparent that this invention can be practiced with a combination of acidic catalysts suited to the peculiarities of a given feed and a given desired produce distribution. In fact, it is within the spirit and scope of this invention to utilize a combination of zeolitic and non-zeolitic acidic cracking catalysts where the feed and product parameters are appropriate. Thus a combination of a large pore zeolite and a medium pore zeolite might well efficiently crack a polystyrene into a wide range $C_6+$ product stream which is high in gasoline boiling range aromatics and yet had a substantial distillate fuel fraction. A combination of zeolitic cracking catalyst and an amorphous cracking catalyst such as conventional petroleum cracking catalyst might be appropriate for converting a bulky plastic product such as a bisphenol, epoxy resin or a polyphenylene oxide into more convenient, lower boiling products.

In any case, suitable zeolitic crystals may be used alone, or in combination with each other, or in combination with non-zeolitic acid catalysts. Suitable zeolites are exemplified by: erionite, offetite, mordenite, faujasite, ZSM-4, ZSM-5, ZSM-11, ZSM-12, ZSM-22, ZSM-23, ZSM-34, ZSM-35, ZSM-50, zeolite L, zeolite beta, zeolite Y, zeolite X, VPI-5, comparably structured SAPO's and their analogues. It should be understood that this list is exemplary and in no way restrictive upon the scope of the zeolitic catalysts for use herein. Non-zeolitic catalysts include clays, acid treated clays, perovskites, layered titanates, silica-alumina, acidic alumina and the like.

Since plastic cracking is a severe service for any catalyst, there being periods of endothermic activity interspersed with regenerative burning/heating treatment, it is preferred to select robust zeolites for use in this invention. Robust zeolites tend to be those which are more siliceous. Acid activity, measured by the Alpha Test, however, tends to be inversely proportional to the proportion of silicon in the zeolite. Thus, a balance must be struck between the acid activity of the zeolite and the robustness, thermal stability, hydrothermal stability and regenerability of the zeolite.

When Alpha Value is examined, it is noted that the Alpha Value is an approximate indication of the catalytic cracking activity of the catalyst compared to a standard catalyst and it gives the relative rate constant (rate of normal hexane conversion per volume of catalyst per unit time). The Alpha Test is described in U.S. Pat. No. 3,354,078; in the *Journal of Catalysis*, Vol. 4, p. 527 (1965); Vol. 6, p. 278 (1966); and Vol. 61, p. 395 (1980), each incorporated herein by reference as to that description. The experimental conditions of the test used herein include a constant temperature of 538° C. and a variable flow rate as described in detail in the *Journal of Catalysis*, Vol. 61, p. 395.

A measure of the stability of a zeolite, and therefore at least its commercial suitability, is its silicon content which may be measured and/or reported as its silica to alumina ratio. In this regard, it must be noted that zeolites have traditionally comprised silicon, aluminum and oxygen with more or less impurity levels of other elements such as iron, boron, gallium and the like. In more recent times, it has been found practical to isomorphously substitute many different elements into the framework structure of a zeolite in substantially ay proportions desired. Thus, the expression "silica to alumina ratio" should be taken as generically describing the proportion of silicon to other non-oxygen framework constituent such as aluminum, iron, boron, gallium, titanium, and the like. The term "silica to alumina ratio" will be used herein in this context and should not be construed as in any way restrictive on the specific composition or compositions of the non-silicon, non-oxygen framework constituent. Thus, silica to alumina ratios of at least about 5 up to about 2000 ore more, depending upon the particular zeolite topology selected, are suitable for use herein.

According to this invention, the zeolitic catalyst may suitably be used in combination with metal catalytic functions in dual functional catalysis. Thus, hydrogenation/dehydrogenation functioning metal catalysts, such as Group VIII metals, may be used. Exemplary metals include platinum, palladium, zinc, nickel, cobalt, magnesium, molybdenum, tungsten, titanium, tantalum, chromium, iron, gallium, mixtures thereof, and other, similarly catalytically active metals. These metals may be incorporated with the zeolite catalyst by any of the conventional techniques known for this purpose, such as impregnation, ion exchange, vapor deposition, co-crystallization, etc.

It is within the scope of this invention that the crystalline acidic zeolite used to catalyze the cracking of plastic materials may be employed as "pure quill", that is unbound, or it may be used in a bound state, both of which being conventional zeolitic catalyst technology. Binders for such catalyst include silica, alumina, silica-alumina, silica-titania, silica-thoria, silica-magnesia, silica-zirconia, silica-beryllia, ternary compositions of silica with other refractory oxides, and the like. Other suitable matrix materials include clays, such as naturally occurring clays illustrated by montmorillonites, kaolines, bentonites, halloysites, dickites, nacrites and anauxites. The proportion of zeolite in a binder/matrix composite may vary from about 1 to 99 weight percent, preferably about 5 to 80 weight percent.

The catalyst of this invention is conveniently in the form of powder, granules or larger particles depending upon the engineering of the particular cracking process employed. Thus a fixed bed will have larger particles than will be fluffed, or fixed/fluidized bed which in turn will have larger particles than fluidized transport bed. Therefore catalyst particle sizes can range from about 0.001 microns up to about ⅛ inch. It will be clear that the cracking process of this invention can be carried out in a fixed, fluffed or transport bed type of reaction zone as desired.

The cracking process should be operated at a temperature high enough to convert the plastic feed from a solid to a fluid state, but not so high as to cause thermal degradation or charring of the plastic. Temperatures in the range of about 200° to 600° C. have been found to be suitable, with temperatures of about 250° to 500° C. being preferred. Of course, the specific reaction temperature must be chosen as a function of the nature of the feed, the particular process, and the product distribution desired. Higher temperatures tend to convert substantially hydrocarbon polymers to a more aromatic product than do lower temperatures. The reaction pressure should be as low as practical since this cracking reaction is more driven by lower rather than higher pressures. However, it does not appear that pressure is a critical process variable, and as such pressures of about 0.1 to 150 atmospheres are suitable.

The cracking process of this invention can be carried out in the effective presence of hydrogen and/or hydrogen contributing compounds. This may be particularly helpful where the plastic feed is hydrogen deficient with respect to the desired product, or the feed contains hetero atoms, such as oxygen, halogen, nitrogen or the like. In using zeolites to catalyze plastic cracking it should be understood that acidic zeolites have a propensity for cleaving hetero atoms, such as oxygen, nitrogen and/or halogens, out of feed materials and condensing them in their fully hydrogenated form. Thus, nitrogen often produces ammonia and oxygen shows up in the product as water. This condensation catalytic activity of zeolites in general, and intermediate pore size zeolites in particular, is often so strong that hydrogen will preferentially partition from the hydrocarbonaceous cracked fragments to the hetero-atom. Thus, it sometimes happens that the hydrocarbonaceous portion of the product may be more hydrogen deficient (i.e. more aromatic) than desired. If coke or coke precursors are produced during the process, hydrogen can react with these components and help keep the catalyst clean in order to maintain its effectiveness for as long as possible. Under those circumstances, as well as others, it thus may be desirable to carry out the plastic cracking process of this invention with augmenting hydrogen, or hydrogen contributing additives. Clearly, where hydrogenation is a desirable reaction in this process, it is preferred to provide a dual functional, cracking/hydrogenation catalyst.

As noted above, cracking reactions are generally endothermic. Heat can be added to the reaction zone in any of several ways. Periodic or continual catalyst regeneration, where deposited carbon is burned off the catalyst, is one known method of bringing heat into the reaction zone. Preheating the feed, or direct, or indirect, heating of the reaction zone is suitable. It is also within the spirit and scope of this invention to heat the reaction zone by simultaneously carrying out an exothermic process therein. Hydrogenation is exothermic and may be used as aforesaid not only to add hydrogen to the product, but also to bring needed heat into the reaction zone. Partial oxidation of the feed, as by cofeeding a limited amount of oxygen or air, will serve to contribute heat to the reaction zone. It is also possible and practical to cofeed one or more suitable reactants to the reaction zone provided the catalyst composition and the operating conditions are such that the cofed reactant will be exothermically converted. Good examples of such cofed reactants are lower alcohols and lower olefins. Most preferably, methanol and/or propylene have been found to be excellent coreactants because they are exothermically converted under plastic cracking conditions and with plastic cracking, acidic zeolite catalysts, to higher hydrocarbons, suitably the same boiling range hydrocarbons sought to be produced by plastic cracking. These coreactants are also relatively hydrogen rich, which may be of assistance in producing an over all product of desired hydrogen to carbon ratio and boiling range.

According to one aspect of this invention, some polymerization reactions have been reported to be catalyzed by suitable metal catalysts supported on zeolitic substrates. Reference is here made to U.S. Pat. No. 4,376,722, commonly assigned herewith, the entire contents of which is incorporated herein by reference. Further, the references cited against such patents are also referred to as disclosing various polymerization processes and catalysts therefor.

In some of these polymerization processes, the catalyst particles leave the process embedded in and as part of the polymer product. Thus, when these polymer products are further processed into films or other shaped articles, they carry the zeolitic based polymerization catalyst with them. Linear low density polyethylene, made by the Unipol process is an excellent example of such a polymer product, and is illustrative of the practice of this aspect of this invention.

Thus, shaped articles made of such zeolite catalyst containing polymers are directly feedable to the process of this invention without the necessity of adding more plastic cracking catalyst thereto. Even if the quantity of the retained zeolitic polymerization catalyst is less than that quantity of catalyst needed for efficient plastic cracking, it will make up part of the cracking catalyst and at least will reduce the amount of fresh zeolitic catalyst that must be supplied to the plastic cracking process hereof.

According to this invention, the plastic (polymer) feed is suitably heated to an appropriate melting temperature, which may also be a temperature at which the solid plastic is converted, and contacted with a zeolitic cracking catalyst in order to carry out the process hereof. It is within the scope of this invention to admix with the plastic feed one or more other materials which will dissolve the plastic or will lower the temperature at which such solid plastic will convert to a fluid form. Most polymers are more or less soluble in their monomers or in compounds which are chemically similar thereto. Hydrocarbonaceous polymers, such as polyethylene, polypropylene, rubbers and the like are often partially or wholly soluble in substantially hydrocarbonaceous liquids, such as distillate fuel oil, naphtha, kerosine and the like. Such dissolved, or partially dissolved plastics make an excellent feed to the instant process.

It has been found to be appropriate to carry out the process of this invention using a proportion of catalyst, based upon the weight of feed, of about 0.01 to 25 %. Preferably a space velocity of about 0.1 to 10 will be sufficient.

This invention will be illustrated by the following examples in which all parts and percentages are by weight unless expressly stated to be on some other basis.

EXAMPLE I

A 5 gram sample of solid ethylene/propylene copolymer was mixed with about ½ gram of ammonium form HZSM-5B particles of about 0.02 micron size. The mixture was heated to 300° C. overnight, thereafter kept at 350° C. for 2 hours and then at 450° C. for 2 hours. The product contained about ½ c.c. of liquid which was subjected to gas chromatographic(GC) analysis as follows:

TABLE 1

| Boiling Range | Weight % |
|---|---|
| 80° C.− | 42.78 |
| 80° C. to 111° C. | 13.62 |
| 111° C. to 144° C. | 14.79 |
| 144° C.+ | 17.11 |

Within this liquid sample, benzene, toluene and xylenes were identified as individual compounds which constituted 1.24, 3.33 and 7.13 weight percent respectively of the liquid product.

EXAMPLE II

A sample of 3 small polyethylene sandwich bags was dissolved in 100 c.c. of benzene at about 60° C. Cooling this solution to room temperature produced a well dispersed slurry, aliquots of which were fed to a series of reaction zones containing in turn ZSM-5B ZSM-12 and nickel ZSM-5A. Several runs were made at various temperatures to produce product as set forth in the following tables. In these tables, the products are reported as a percentage of the total liquid or gas product respectively collected. Of course benzene, being the solvent and carrier, was the overwhelming component of the liquid product.

TABLE 2

| | Catalyst + ZSM-5B | |
|---|---|---|
| Temperature °C. | 450 | 500 |
| Liquid Product | | |
| Light ends | 0.047 | 0.017 |
| Benzene | 98.475 | 99.067 |
| Toluene | 0.489 | 0.479 |
| Ethyl Benzene | 0.711 | 0.335 |
| Xylenes | 0.061 | 0.070 |
| Cumene | 0.039 | 0.009 |
| n-Propylbenzene | 0.072 | 0.024 |

TABLE 2A

| Gaseous Products | | |
|---|---|---|
| Carbon Monoxide | 45.767 | 28.485 |
| Methane | 11.965 | 27.237 |
| Ethane | 6.267 | 11.962 |
| Carbon Dioxide | 23.133 | 13.803 |
| Ethylene | 1.001 | 10.363 |
| Propane | 9.953 | 6.141 |
| Propylene | 1.913 | — |

TABLE 3

| | catalyst = N$_i$ZSM-5A | | |
|---|---|---|---|
| Temperature °C. | 400 | 450 | 500 |
| Liquid Product | | | |
| Light Ends | 0.801 | .0 | 0.005 |
| Benzene | 98.184 | 99.963 | 99.956 |
| Toluene | 0.015 | 0.037 | 0.039 |

TABLE 4

| | Catalyst = ZSM-12 | | |
|---|---|---|---|
| Temperature °C. | 400 | 450 | 500 |
| Liquid Products | | | |
| Light Ends | 0.015 | 0.012 | — |
| Benzene | 99.269 | 79.806 | 99.634 |
| Toluene | 0.444 | 0.930 | 0.257 |

TABLE 4-continued

| | Catalyst = ZSM-12 | | |
|---|---|---|---|
| Temperature °C. | 400 | 450 | 500 |
| Ethyl Benzene | 0.193 | 0.491 | 0.075 |
| Cumene | 0.007 | — | — |
| n-Propyl Benzene | 0.008 | 0.014 | 0.014 |
| Higher Hydrocarbons | — | 0.746 | — |

What is claimed is:

1. A process for converting a polyolefin, said polyolefin having been made by catalytic polymerization of at least one alpha olefin with a catalyst comprising a zeolite which zeolite remains with the polymerization product, to lower molecular weight products, comprising normally fluid hydrocarbons, which comprises: contacting such polyolefin with at least one acidic catalyst, comprising a zeolite provided at least in part by said polymerization catalyst, at a pressure and at an elevated temperature sufficient to convert said polyolefin to a fluid state and for a time sufficient to effect a catalytic cracking of said fluid state polyolefin; and recovering therefrom a product comprising normally fluid hydrocarbons.

2. A process for converting a polymer having been made by catalytic polymerization with a catalyst comprising a zeolite which zeolite remains with the polymerization product, to lower molecular weight products, comprising normally fluid hydrocarbons, which comprises: contacting such polymer with at least one acidic catalyst, comprising a zeolite provided at least in part by said polymerization catalyst, at a pressure and at an elevated temperature sufficient to convert said polymer to a fluid state and for a time sufficient o effect catalytic cracking of aid fluid state polymer; and recovering therefrom a product comprising normally fluid hydrocarbons.

3. A process as claimed in claim 2 wherein said polymer is normally solid.

4. A process as claimed in claim 3 wherein said pressure and temperature are sufficient to convert said solid polymer to a fluid, but insufficient to thermally degrade said fluid state polymer.

5. A process as claimed in claim 2, carried out at about 200° to 600° C.

6. A process as claimed in claim 2 including dissolving at least some of said polymer in a solvent therefor.

7. A process as claimed in claim 2, wherein said catalyst comprises at least one crystal having the topology of ZSM-4, ZSM-5, ZSM-11, ZSM-12, ZSM-22, ZSM-23, ZSM-34, ZSM-35, ZSM-50, zeolite beta, zeolite L, zeolite X, zeolite Y, erionite, offretite, mordenite, faujasite and VPI-5.

8. A process as claimed in claim 7 wherein said catalyst comprises a mixture of zeolites.

9. A process as claimed in claim 2 wherein said catalyst comprises a mixture of said zeolite and at least one non-zeolitic acidic cracking catalyst.

10. A process as claimed in claim 7 wherein said catalyst comprises, in addition to said zeolite, at least one catalytic metal.

11. A process as claimed in claim 10 wherein said metal is at least one of platinum, palladium, nickel, cobalt, iron, zinc, magnesium, molybdenum, tungsten, titanium, gallium, tantalum and chromium.

12. A process as claimed in claim 2 wherein said zeolitic catalyst comprises a refractory oxide binder matrix.

13. A process as claimed in claim 12 wherein said binder matrix comprises at least one of silica, alumina, silica-alumina, silica-titania, silica-thoria, silica-magnesia, silica-zirconia and silica-beryllia.

14. A process as claimed in claim 2 wherein said zeolitic catalyst has an acid activity corresponding to an alpha of at least about 0.5.

15. A process as claimed in claim 2 wherein said zeolite has a silica to alumina ratio of about 5 to 2000.

16. A process as claimed in claim 2 comprising cofeeding hydrogen or a source of hydrogen to said reaction zone.

17. A process as claimed in claim 16 including said catalyst comprising at least one metal hydrogenation catalyst.

18. A process as claimed in claim 2, including cofeeding an additional convertible reactant to said reaction zone, which additional reactant is exothermically converted under the conditions of endothermic polymer conversion in contact with the same catalyst sufficient to provide at least part of heat required by said endothermic cracking.

19. A process as claimed in claim 18 wherein said additional convertible reactant is oxygen and cofeeding said oxygen in less than a stoichiometric quantity.

20. A process as claimed in claim 9 wherein said non-zeolitic catalyst component comprises at least one amorphous refractory oxide.